United States Patent [19]
Lönnqvist et al.

[11] Patent Number: 5,504,577
[45] Date of Patent: Apr. 2, 1996

[54] METHOD AND APPARATUS FOR MEASURING METEOROLOGICAL VISIBILITY AND SCATTERING OF LIGHT, SAID APPARATUS UTILIZING COMMON OPTICS FOR TRANSMISSION AND RECEPTION

[75] Inventors: Jan Lönnqvist, Espoo, Finland; Horst Hüttmann, Uetersen, Germany

[73] Assignee: Vaisala Oy, Helsinki, Finland

[21] Appl. No.: 502,604

[22] Filed: Jul. 14, 1995

Related U.S. Application Data

[63] Continuation of Ser. No. 91,446, Jul. 15, 1993, abandoned.

[30] Foreign Application Priority Data

Jul. 30, 1992 [FI] Finland ............................ 923432

[51] Int. Cl.⁶ .......................................... G01N 21/00
[52] U.S. Cl. ....................... 356/342; 356/5.06; 342/26
[58] Field of Search ........................... 356/335–342, 356/343, 4, 5, 28.5, 152, 5.01, 5.06; 250/574, 573, 575; 340/601, 602; 342/26; 359/509, 512, 154, 180, 189

[56] References Cited

U.S. PATENT DOCUMENTS

| | | | |
|---|---|---|---|
| 3,430,047 | 2/1969 | Hurkamp | 359/189 |
| 4,397,549 | 8/1983 | Morgan | 356/342 |
| 4,605,302 | 8/1986 | Lofgren et al. | 356/5 |
| 4,722,599 | 2/1988 | Fruengel et al. | 356/342 |
| 4,931,767 | 6/1990 | Albrecht et al. | 356/342 |
| 5,116,124 | 5/1992 | Hüttmann | 356/342 |

FOREIGN PATENT DOCUMENTS

| | | |
|---|---|---|
| 0358507 | 9/1989 | European Pat. Off. . |
| 473495 | 3/1992 | European Pat. Off. . |
| 2594535 | 8/1987 | France . |

*Primary Examiner*—Hoa Q. Pham

[57] ABSTRACT

The invention concerns a method and device for measuring the meteorological visibility and the scattering of light. A light pulse is emitted into the atmosphere via an optical transmit system, the backscattered light returns via the optical transmit system after which its intensity and delay are measured. The waveform of the optical transmit pulse generated at the instant of its launching from within the apparatus is sensed in a manner that excludes any backscattered light originating from outside the measurement system, this signal is scaled for both its magnitude and phase so as to achieve a suitable feedback signal relative to the actual measurement signal and said feedback signal is subtracted from said measurement signal to avoid overloading of the receiver.

21 Claims, 6 Drawing Sheets

METHOD AND APPARATUS FOR MEASURING METEOROLOGICAL VISIBILITY AND SCATTERING OF LIGHT, SAID APPARATUS UTILIZING COMMON OPTICS FOR TRANSMISSION AND RECEPTION

This application is a continuation of application Ser. No. 08/091,446 filed on Jul. 15, 1993, now abandoned.

The present invention relates to a method for measuring meteorological visibility and scattering of light and the calibration thereof.

The invention also concerns an apparatus for measuring meteorological visibility and scattering of light and the calibration thereof.

BACKGROUND ART

EP patent application 89309088.6 (Vaisala Oy) Laid-Open Publication No. EP 0358507, describes a measurement system for the scattering of light, in which system the active surface of the transmitter and the receiver is formed into a single surface by means of, e.g., combined optical fiber bundles.

FR patent application 2,594,535 also discloses an embodiment similar to that described above.

Despite the significant benefits achieved by using a common active surface for both the transmitting and receiving systems via a single optical system, unexpected problems have been encountered. As the transmitted pulse has an extremely high peak intensity, the optical fibers of the transmitting system permit stray coupling to the adjacent fibers of the receiving system, whereby the receiver input amplifier is temporarily overloaded. This can cause problems particularly in near-range scattering measurement, since the receiver input amplifier is nonresponsive during the very time the near-range reflected information should typically be detected by the receiver.

The same problem is also encountered in the conventional embodiments based on a beam splitter that have the further drawback of a partial loss of transmit power in the beam-splitting optical system.

OBJECTIVES OF THE INVENTION

It is an object of the present invention to overcome the disadvantages related to the above-described prior-art techniques and to achieve an entirely novel method and apparatus for the measurement of the scattering of light, said apparatus using a common optical system for both transmission and reception.

SUMMARY OF INVENTION

The invention is based on adapting a second photoresponsive feedback element into the measurement system in such a point of the system that receives the transmitted optical signal at the same power level as the system receiver proper receives the stray signal owing to the optical stray coupling, while the feedback element receives none of the optical signal imposed on the system by external reflections or backscatter. The receiving element proper and the feedback element should be as identical as possible both in sensitivity and response time.

The invention offers significant benefits.

The invention makes it possible to avoid overloading of the receiver proper immediately after the transmitted pulse, which significantly improves measurements, particularly in the near range. Furthermore, errors in far-range measurements are reduced.

The foregoing and other objectives of the present invention will become more apparent from the detailed description give hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention and wherein.

Figure 1:
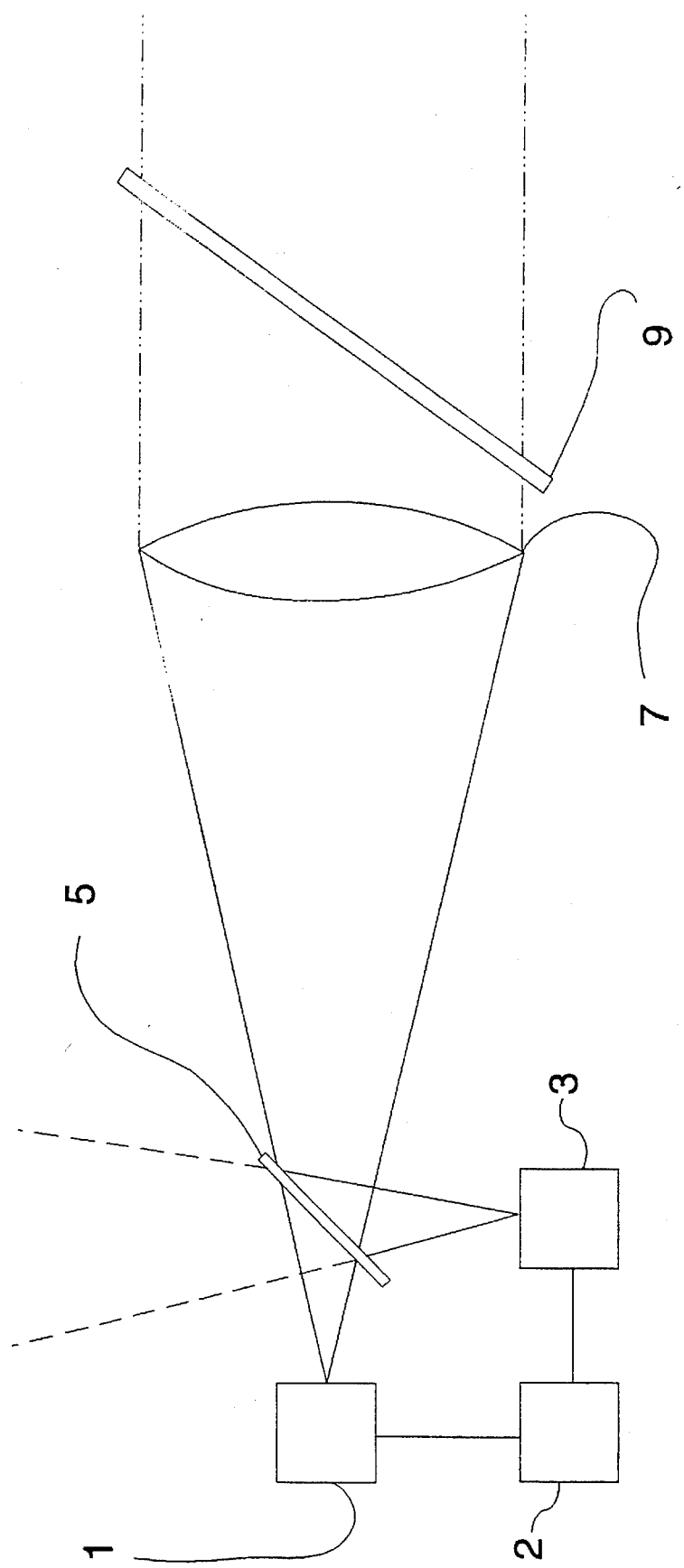
FIG. 1 shows diagrammatically a measurement system based on a beam splitter of conventional technology.

With reference to FIG. 1, an optical measurement system based on a beam splitter comprises a transmitter 1, from which an optical pulse is emitted via a beam splitter 5 to a lens 7, which launches the light pulse to a desired spatial angle. A window 9 is employed to prevent contamination of the optical element 7. After the light pulse launched from the optical element 7 propagates along a path until it meets an obstacle, a portion of the light is backscattered along the same path, whereby the beam splitter 5 guides the returning light to a receiver 3. Adapted to the receiver 3 is also a unit 2 which is synchronized to the transmitter 1 and is capable of determining the delay and intensity of the return pulse, whereby such information can be utilized to define the object from which the reflection of the optical signal takes place. Owing to the high peak intensity of the transmitted pulse, imperfections of the beam splitter 5 impose a direct stray signal onto the receiver 3. Due to the low intensity of the return signal, the input amplifier of the receiver 3 must have a high gain, whereby the above-mentioned stray signal typically overloads the input amplifier of the receiver 3. Stray signals with a short delay are also imposed onto the received return signal due to reflections from the lens 7 and the window 9.

Figure 2:
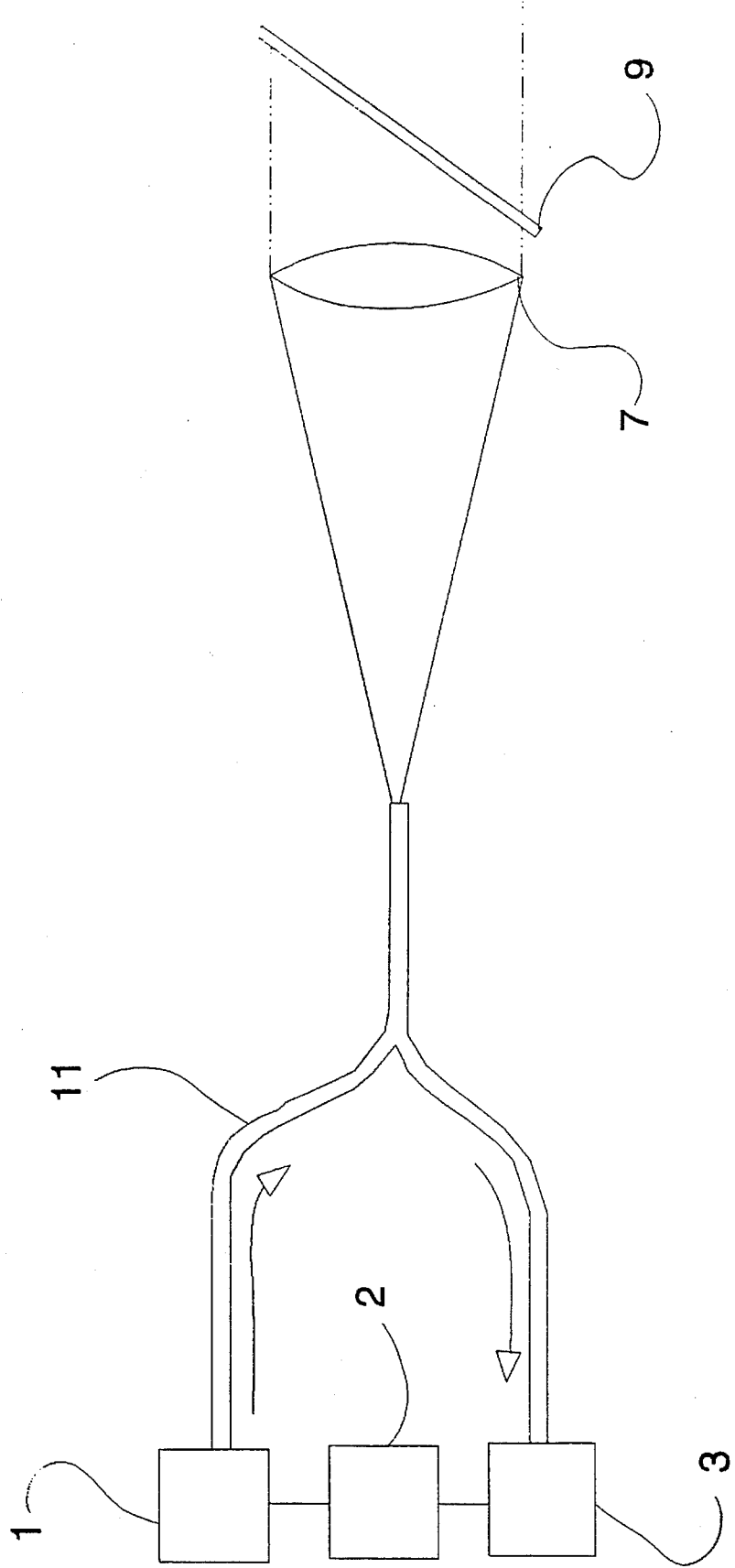
FIG. 2 shows diagrammatically a conventional measurement system based on a Y-coupler implemented with the help of optical fibers.

With reference to FIG. 2, measurement using a Y-coupler 11 implemented by means of optical fibers takes place in the same manner as in the embodiment illustrated in FIG. 1. In this embodiment the beam splitter is replaced by a Y-coupler 11, which achieves a better directional gain for guiding the optical measurement signal to the desired object, since the losses by the upward reflection (cf. FIG. 1) caused by the beam splitter are avoided. However, the Y-coupler 11 has a drawback of optical signal stray coupling within the common part of the divider directly into the receiver input fibers during the transmission of the outgoing pulse. Hence, similar problems are involved as those discussed in conjunction with FIG. 1.

Figure 3:
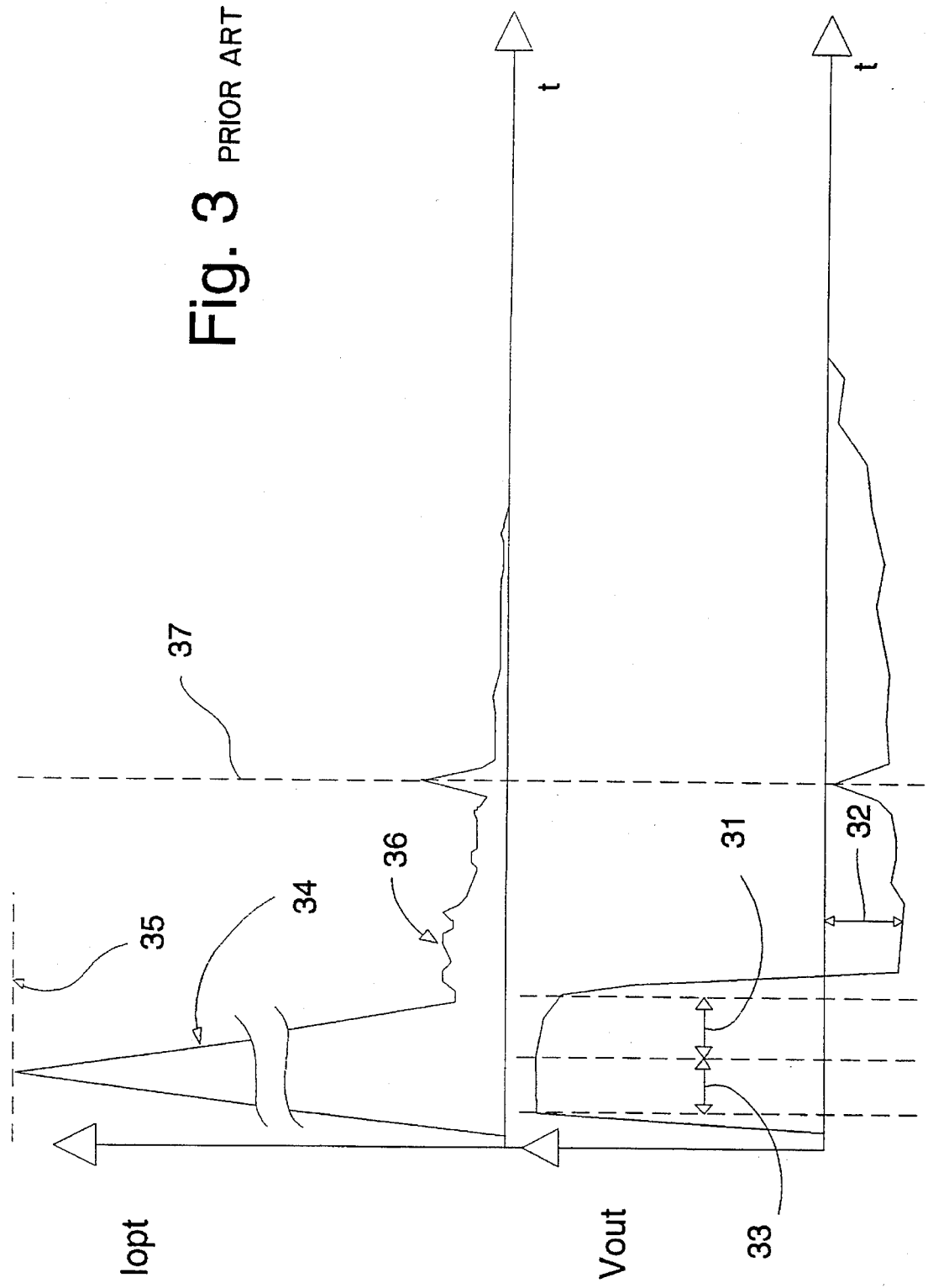
FIG. 3 shows in a graph the received optical input signal and the corresponding electrical output signal of the measurement system illustrated in FIGS. 1 and 2.

The upper diagram of FIG. 3 shows the optical input of a receiver. The optical stray signal caused by the above-described reasons at the start of the measurement cycle loads the receiver input with a transient pulse signal 34 of approx. 1000–. . . 1,000,000-fold intensity 35 compared with the normal signal level. According to the lower diagram depicting the output signal of the receiver, said transient pulse signal 34 drives the receiver input amplifier into saturation during the period 33. During the period 31 the amplifier recovers from saturation, and though a backscatter input signal component 36 caused by mist is present, it cannot be detected from the amplifier output signal due to overload distortion 32. At instant 37 a reflection from a cloud or fixed object is present in the input signal. As is evident, also this later arriving signal can be corrupted by the overload distortion 32.

Figure 4:
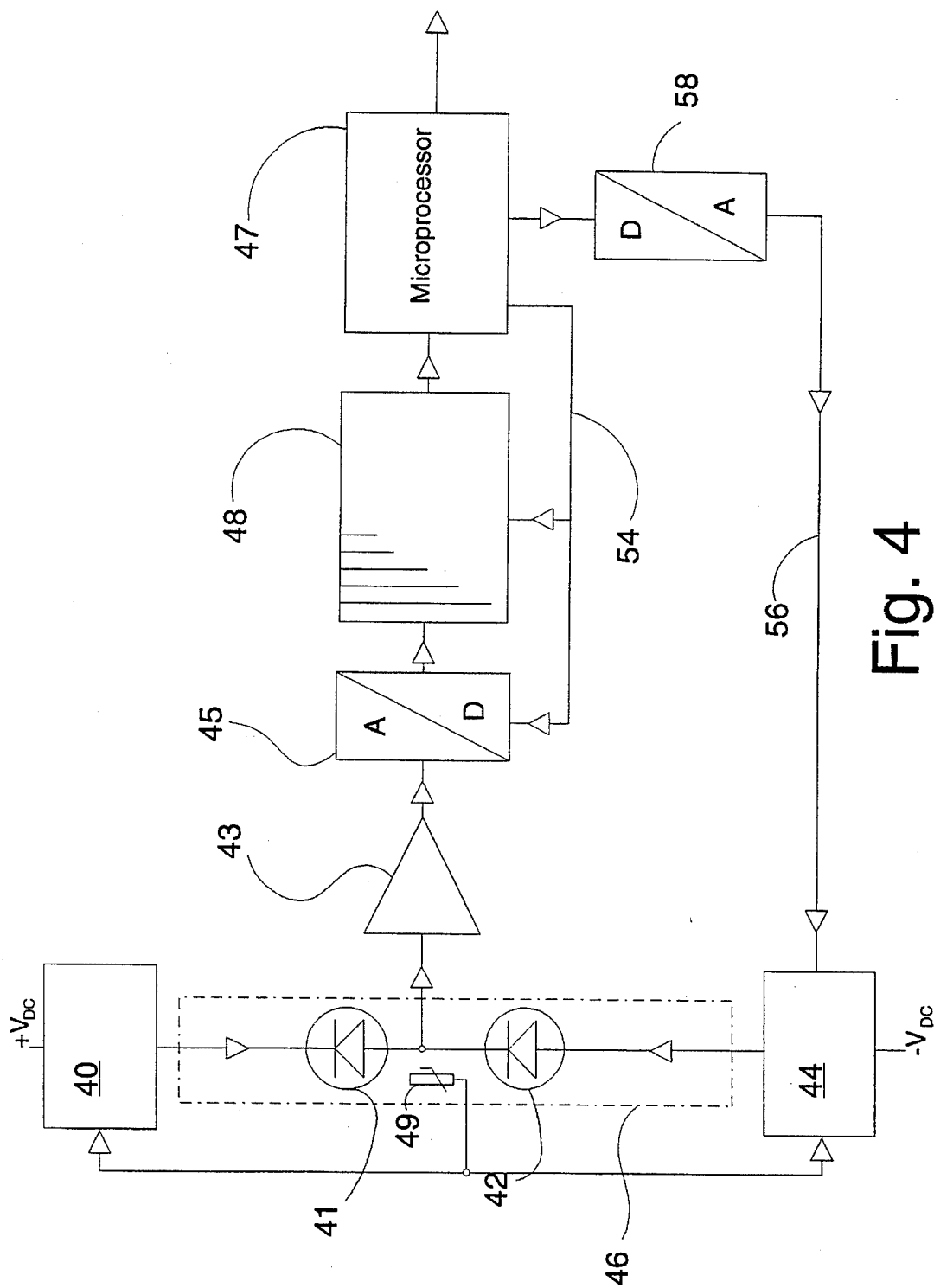
FIG. 4 shows a block diagram of the apparatus according to the invention.

With reference to FIG. 4, amplifier overload can be avoided by configuring a conventional photoresponsive element 41 into a half-bridge with feedback element 42. In the embodiment illustrated in the diagram the photoresponsive elements 41 and 42 are reverse-biased avalanche photodiodes. When a high-intensity optical pulse impinges on both diodes 41 and 42 simultaneously, the stray signal coupled via optical stray coupling is canceled almost entirely. Bias adjustment of half-bridge permits fine-adjustment of the compensating effect of the feedback photodiode 30 to a degree of substantially perfect cancellation of the transient signal resulting from optical stray coupling. Such arrangement achieves protection against overloading of the amplifier 43. The bias voltage can be continuously controlled by first converting the analog measurement signal into digital form with the help of an A/D converter 45 and then processing its digital output signal in an information processing unit 47. The A/D converter 45 used is typically a so-called FLASH converter operating with a sampling interval of 50 ns and resolution of 8 bits. Prior to being taken to the microprocessor 47, the output signal of the A/D converter 45 is loaded in a FIFO (First-In/First-Out) register memory 48. The length of the intermediate register memory 48 can be, e.g., 512 samples. The microprocessor 47 is employed for controlling the sampling operation via a bus 54 which is connected to both the intermediate register memory 48 and the A/D converter 45. The fine-adjustment of the bias voltage is implemented through digitally steering from the information processing unit 47 a bias voltage generator 44 which controls the bias voltage over the photodiodes 41 and 42. The bias voltage control can be performed continuously without delay as the information processing unit senses the deviations in the stray signal cancellation accuracy of the measurement signal and can thus differentially either increase or decrease the bias voltage so as to achieve perfect stray signal cancellation. In practice the bias voltage control is implemented by means of a constant-voltage regulator 40 connected to the positive supply voltage and an adjustable voltage regulator 44 which is connected to the negative supply voltage and receives its control voltage from the microprocessor 47 over the bus 56 via a D/A converter 58. The half-bridge 46 is advantageously complemented with a temperature-compensating circuit 49 which controls the voltage regulators 40 and 44. Thus, the half-bridge 46 formed by the diodes 41 and 42 can be considered a subtracting circuit which cancels the stray signal component from the measurement signal.

Figure 5:
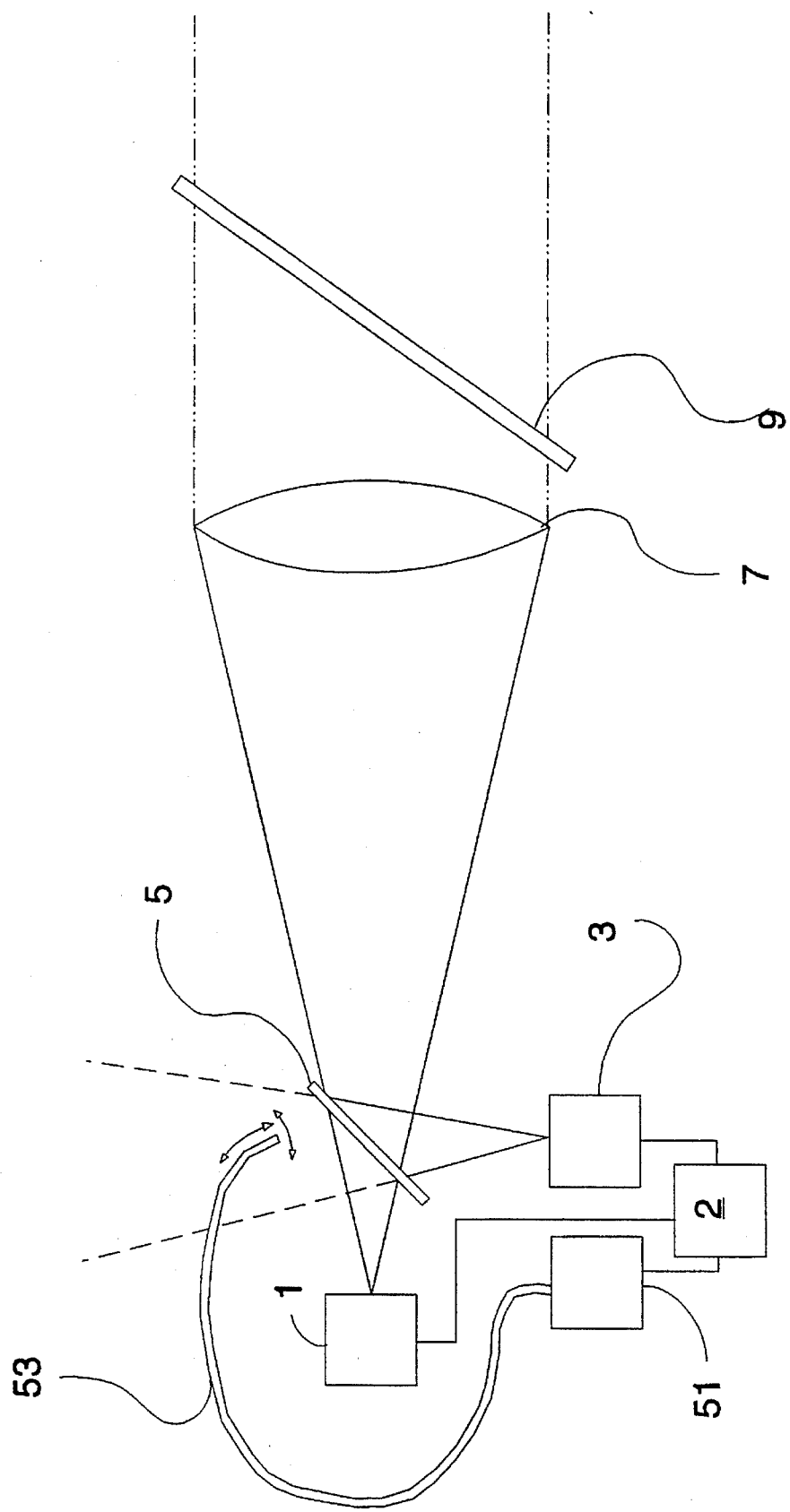
FIG. 5 shows an arrange according to the invention adapted to the basic embodiment illustrated in FIG. 1.

With reference to FIG. 5, the feedback of the optical signal in system based on a beam splitter 5 is implemented by means of an optical fiber 53 optically coupled to a feedback sensor element 51. The free end of the fiber 53 is placed to the opposite side of the beam splitter 5 relative to the receiver element 3. The length of the fiber 53 can be selected so that it produces a delay matching the delay of the most significant stray signal component. For instance, if the strongest stray signal component originates from the beam splitter, the delay caused by the fiber 53 must be adjusted to the delay on the optical path between the receiver 3 and the beam splitter. If the strongest stray signal component originates from the focusing lens 7 (or lens group), the delay caused by the fiber 53 must be adjusted to twice the delay on the optical path from the beam splitter 5 to the lens 7. By virtue of the optical fiber 53, the photoresponsive elements proper can be placed maximally tight to each other, whereby these elements can be kept in maximally identical ambient conditions. The free end of the fiber 53 can be made movable, thereby giving a further means of stray signal cancellation adjustment through moving the free end of the fiber 53, thus complementing the bias voltage control discussed above in conjunction with FIG. 4. In practice the coarse adjustment is made mechanically bending the fiber end and then performing fine-adjustment by electronic means.

Figure 6:
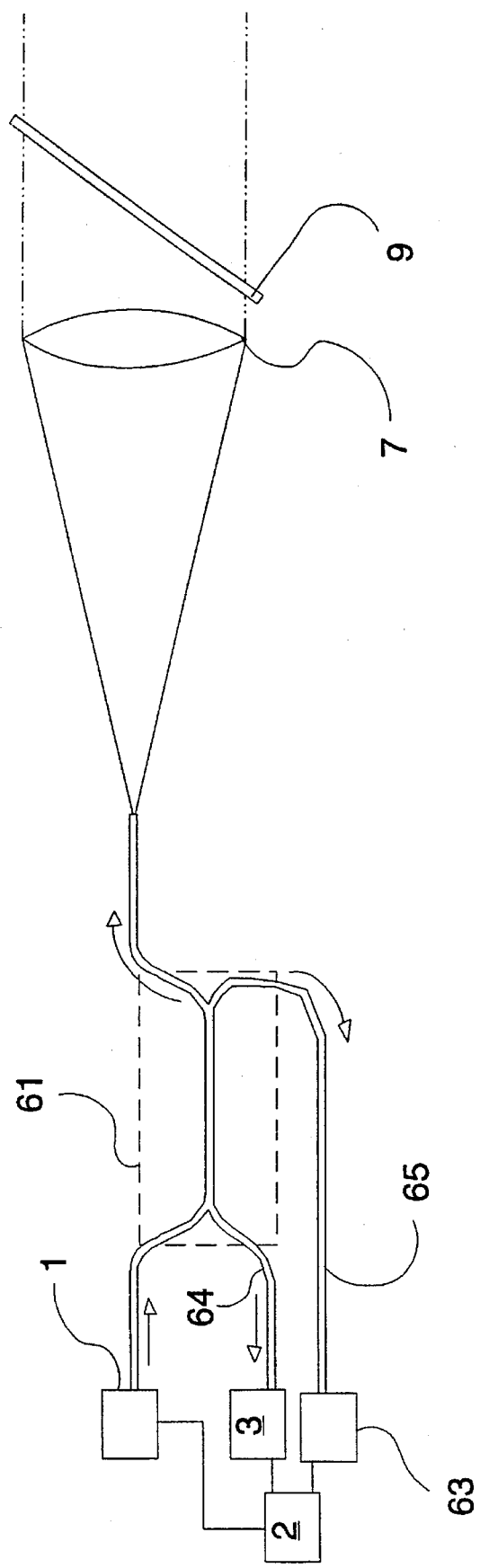
FIG. 6 shows an arrangement according to the invention adapted to the basic embodiment illustrated in FIG. 2.

With reference to FIG. 6, the feedback signal can be taken via an optical power divider 61 when a Y-coupler is used. The power division ratio can be 2:2, for instance. To optimize the feedback effect, the delay caused by the feedback fiber 65 between the optical power divider and the feedback signal sensor element 63 is adjusted essentially equal to the delay caused by the fiber 64 connecting the receiver 3 to the optical power divider 61.

In the preferred embodiments the feedback sensor element is only used for measuring the stray signal component stemming from the optical stray coupling, particularly its waveform, which is scaled and equal phased prior to its subtraction from the uncorrected output signal of the receiver proper.

Consequently, deviating from the implementation shown in FIG. 4, it is also possible within the scope of the invention to implement the feedback arrangement by means of separate sensors, which are used for the cancellation of the optical stray coupling after, e.g., a separate calibration step.

The compensation of different delays can alternatively be arranged by means of digital delay circuits placed after the A/D converter, whereby both the measurement and the feedback signal can be delayed as necessary.

The invention is particularly suited for use in conjunction with a Y-coupler implemented with optical fibers, while substantial benefits are also achieved in conjunction with measurement systems based on beam splitters illustrated in FIGS. 1 and 5.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for measuring meteorological visibility and light scattering comprising the steps of:

emitting a light pulse into an atmosphere via an optical transmit system;

determining intensity and delay of a received backscattered light signal returned via the optical transmit system;

sensing a waveform of a transient pulse generated within the optical transmit system in conjunction with launching of the transmit pulse in a manner that excludes any backscattered light originating from outside the system;

said sensed waveform being scaled for both its magnitude and phase so as to form a suitable feedback signal relative to the received backscattered light signal, and subtracting said feedback signal from said backscattered light signal, to avoid overloading of the receiver.

2. A claim as defined in claim 1 wherein:

an intensity of the sensed waveform is scaled by half-bridge connected avalanche photobodies, whose bias voltage is controlled in order to obtain a suitable feedback signal.

3. A method as defined in claim 2, wherein:

the received signal enters a receiver via a beam splitter, and the sensed waveform is sensed via an optical fiber whose first end is placed to an opposite side of the beam splitter relative to the receiver and whose second end is coupled to a feedback signal sensor.

4. A method as defined in claim 2, wherein:

the received signal enters a receiver via a Y-coupler, and the sensed waveform is sensed via an optical power divider which includes said Y-coupler and thus couples the received signal to the feedback sensor.

5. An apparatus for measuring the meteorological visibility and the scattering of light, said apparatus comprising:

transmission means for generating a transmit light pulse;

an optical transmit system for launching said transmit light pulse into an atmosphere;

receive means for measuring intensity of a backscattered light signal which travels back via said optical transmit system;

delay-measuring means for measuring propagation delay of said backscattered light;

feedback means for measuring a waveform of an optical transient pulse generated within the apparatus in conjunction with the launching of the transmit pulse, the measurement being performed in a manner that excludes any backscattered light originating from outside the measurement system;

scaling means for scaling the waveform measured by said feedback means so as to form a suitable feedback signal relative to the measured backscattered signal; and subtraction means for subtracting said feedback signal from said measured backscattered signal to avoid overloading of the receive means.

6. An apparatus as defined in claim 5, wherein said subtraction means comprise:

a half-bridge including a measuring diode and a feedback-sensing photodiode;

and said scaling means comprising a bias voltage control element for said half-bridge.

7. An apparatus as defined in claim 6, said apparatus having a beam splitter for routing the backscattered signal traveling back via said optical transmit system to said receive means;

and an optical fiber whose first end is placed to an opposite side of the beam splitter relative to the receive means and a second end of the fiber is coupled to a feedback signal sensor employed for measuring the waveform of the transient pulse generated with the apparatus.

8. An apparatus as defined in claim 6, said apparatus having a Y-coupler for routing the backscattered signal traveling back via said optical transmit system to said receive means;

and an optical power splitter coupled to a feedback signal sensor employed for measuring the waveform transient pulse generated within the apparatus.

9. In a system for transmitting and receiving light pulses, a method for calibrating measurement of meteorological activity and light scattering to eliminate distortion due to stray signals, comprising the steps of:

transmitting an output light pulse;

measuring stray light signals from the output pulse prior to the output pulse leaving the system to thereby enter an ambient environment, the stray light signals including direct stray light signals directly received without having been reflected, without leaving the system and therefore without having been backscattered by the ambient environment;

receiving an input light pulse, the input pulse being a backscatter of the output pulse from the ambient environment; and calibrating the input pulse to form a calibrated pulse as a function of the stray signals, to eliminate distortion due to the stray signals.

10. A method as in claim 9, wherein the step of calibrating includes:

subtracting the stray light signals from the input pulse to form the calibrated pulse.

11. A method as in claim 9, wherein the step of calibrating includes:

scaling an intensity and delay of the stray light signals.

12. An apparatus for calibrating measurement of meteorological activity and light scattering to eliminate distortion due to stray signals having a transmitter for transmitting an output light pulse into an ambient environment and a receiver for receiving an input light pulse backscattered by the ambient environment, comprising:

a sensor for measuring stray light signals from the output light pulse prior to the output light pulse leaving the apparatus to thereby enter the ambient environment, and producing feedback signals, the stray light signals including direct stray light signals directly received without having been reflected, without leaving the system and therefore without having been backscattered by the ambient environment; and a calibrater for calibrating the input light pulse to form a calibrated pulse as a function of the feedback signals, to eliminate distortion due to the stray light signals.

13. A apparatus as in claim 12, wherein the calibrator includes:

a subtracter for subtracting the stray light signals from the input pulse to form the calibrated pulse.

14. A apparatus as in claim 12, wherein the apparatus further includes:

a beam splitter having a first and second side, for splitting the input pulse off a path shared by the output pulse to the first side;

wherein the receiver also receives direct stray signals on the first side of the beam splitter, without leaving the system and therefore without having been backscattered by the ambient environment, due to imperfections in the beam splitter;

wherein the stray signals include output pulse losses from the second side of the beam splitter, due to imperfections in the beam splitter;

the apparatus further includes an optical connector for optically transmitting the output pulse losses to the sensor, wherein the measured stray signals are output pulse losses.

15. A apparatus as in claim 12, further comprising:

an optical power divider; and an optical feedback path from the power divider to the sensor;

wherein the stray signals include stray coupling signals from the power divider, the coupling signals being measured by the sensor to form the feedback signals.

16. A apparatus as in claim 12, wherein:

the calibrater scales an intensity and delay of the stray light signals.

17. An apparatus for calibrating measurement of meteorological activity and light scattering to eliminate distortion due to stray light signals having a transmitter for transmitting an output light pulse into an ambient environment and a receiver for receiving an input light pulse backscattered by the ambient environment, comprising:

a beam splitter, having a first and second side, splitting the input light pulse off a path shared by the output light pulse, the output light pulse reflecting off a first side of the beam splitter and the input light pulse being output the second side of the beam splitter;

a sensor for measuring stray light signals from the output light pulse prior to the output light pulse leaving the apparatus to thereby enter the ambient environment, and producing feedback signals, the sensor including an optical element on the second side of the beam splitter for receiving stray light signals from the output light pulse passing through the beam splitter; and a calibrater for calibrating the input light pulse to form a calibrated pulse as a function of the feedback signals, to eliminate distortion due to the stray light signals.

18. An apparatus for calibrating measurement of meteorological activity and light scattering to eliminate distortion due to stray light signals having a transmitter for transmitting an output light pulse into an ambient environment and a receiver for receiving an input light pulse backscattered by the ambient environment, comprising:

an optical power divider forming a portion of the optical path for the output light pulse and for the input light pulse;

a sensor for measuring stray light signals from the output light pulse prior to the output pulse leaving the apparatus to thereby enter the ambient environment, and producing feedback signals, the sensor including an optical element integrally connected to the optical power divider; and a calibrater for calibrating the input light pulse to form a calibrated pulse as a function of the feedback signals, to eliminate distortion due to the stray light signals.

19. In a system for transmitting and receiving light pulses, a method for calibrating measurement of meteorological activity and light scattering to eliminate distortion due to stray signals, comprising the steps of:

transmitting an output light pulse;

measuring stray light signals from the output light pulse prior to the output light pulse leaving the system to thereby enter an ambient environment;

receiving an input light pulse, the input light pulse being a backscatter of the output light pulse from the ambient environment; and calibrating the input light pulse to form a calibrated pulse as a function of the stray light signals, to eliminate distortion due to the stray light signals, and said step of calibrating including scaling an intensity and delay of the stray light signals.

20. A method as in claim 19, wherein:

the stray light signals include exclusively internally reflected signals reflected without leaving the system and therefore without having been backscattered by the ambient environment.

21. An apparatus for calibrating measurement of meteorological activity and light scattering to eliminate distortion due to stray light signals having a transmitter for transmitting an output light pulse into an ambient environment and a receiver for receiving an input light pulse backscattered by the ambient environment, comprising:

a sensor for measuring stray light signals from the output pulse prior to the output light pulse leaving the apparatus to thereby enter the ambient environment, and producing feedback signals; and a calibrater for calibrating the input light pulse to form a calibrated pulse as a function of the feedback signals, to eliminate distortion due to the stray light signals and said calibrator scaling an intensity and delay of said stray light signals.

* * * * *